Figure 1:
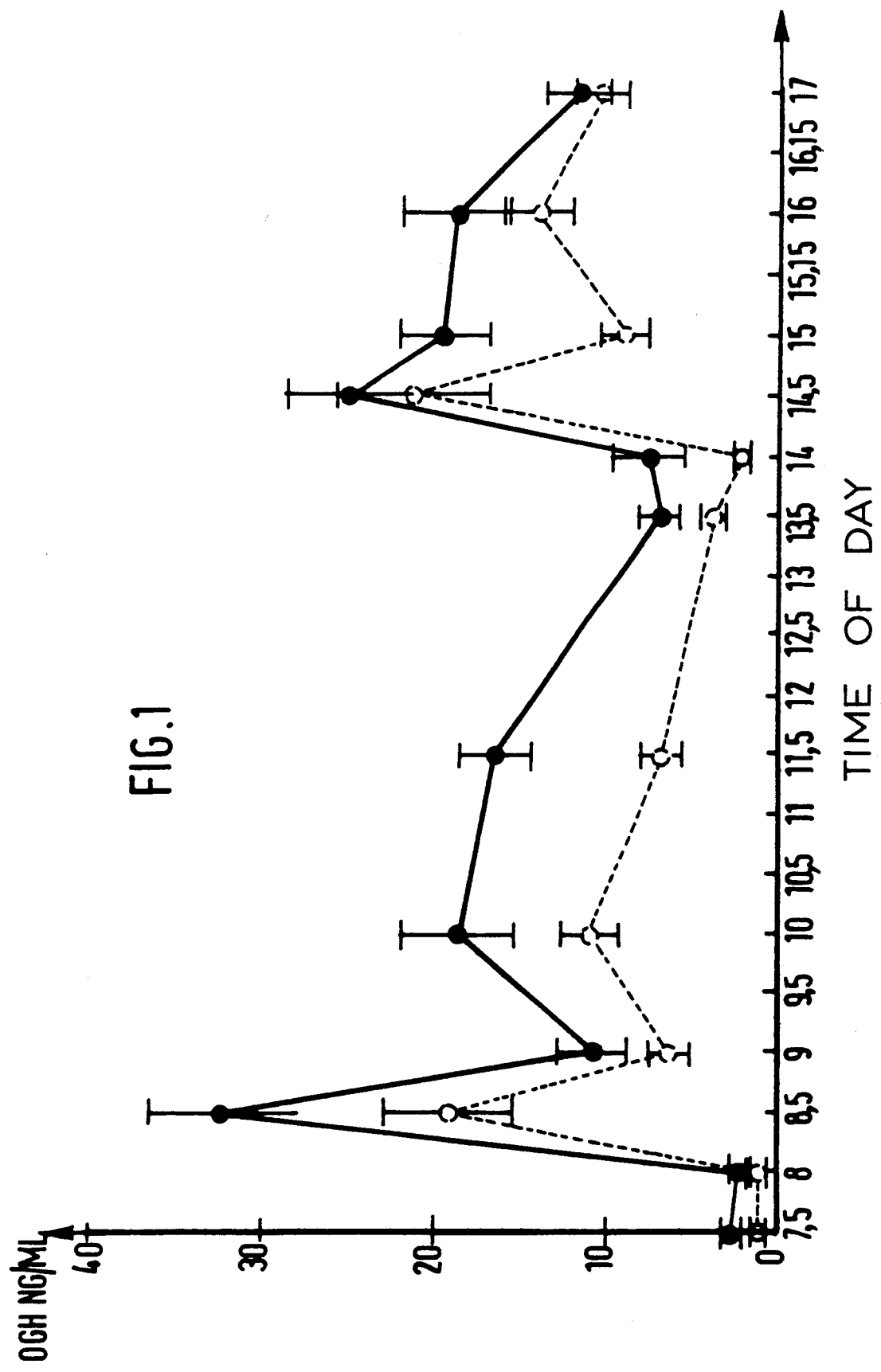

United States Patent [19]

Kann et al.

[11] Patent Number: 5,061,690

[45] Date of Patent: Oct. 29, 1991

[54] METHOD FOR INCREASING MILK PRODUCTION IN MAMMALS AND/OR INCREASING THE BIRTH WEIGHT OF THEIR NEWBORN AND IMPROVING POSTNATAL GROWTH

[75] Inventors: Guy Kann, Boulogne; Jack Martinet, Vieille Eglise, both of France

[73] Assignee: Institut National de la Recherche Agronomique, Paris, France

[21] Appl. No.: 574,434

[22] Filed: Aug. 28, 1990

Related U.S. Application Data

[63] Continuation of Ser. No. 266,087, Nov. 2, 1988, abandoned.

[30] Foreign Application Priority Data

Nov. 4, 1987 [FR] France ............................... 87 15313

[51] Int. Cl.$^5$ ............................................. A61K 37/43
[52] U.S. Cl. ..................................... 514/12; 530/324; 530/399
[58] Field of Search ................... 514/12; 530/324, 399

[56] References Cited

U.S. PATENT DOCUMENTS 4,585,756 4/1986 Brazeau, Jr. et al. ................. 514/12

OTHER PUBLICATIONS

Guillemin et al., Science, vol. 218, pp. 585–587, 1982.
Baird et al., CA 102:125984e, 1985.

*Primary Examiner*—John Doll
*Assistant Examiner*—Choon P. Koh
*Attorney, Agent, or Firm*—Frost & Jacobs

[57] ABSTRACT

Method for increasing milk production in mammals including man, and/or for increasing the birth weight of their newborn and improving postnatal growth, according to which the female mammal is supplied during pregnancy with an effective amount of hGRF or of one of its analogs, or alternatively of an active fragment of hGRF or of one of its analogs.

The treatment is of short duration, for example from 10 to 20 days. Its effects are lasting and extend throughout the lactation period.

Application to the treatment of animals of ovine, caprine, bovine or porcine species.

6 Claims, 5 Drawing Sheets

METHOD FOR INCREASING MILK PRODUCTION IN MAMMALS AND/OR INCREASING THE BIRTH WEIGHT OF THEIR NEWBORN AND IMPROVING POSTNATAL GROWTH

This is a continuation of now abandoned application Ser. No. 07/266,087, filed Nov. 2, 1988.

The present invention relates to improving milk production in mammals, including man, as well as to increasing the birth weight of their newborn and to improving their postnatal growth. The invention applies, in particular, to animals of the ovine, caprine, bovine and porcine species.

In relation to milk production, the effects of bovine growth hormone (hereinafter designated by the abbreviation "bGH"), obtained by genetic recombination, on lactation in dairy cows have been studied by Bauman D. E. et al, whose work has been reported in "J. Dairy Sci., 65 (suppl 1) 121 (Abst.), 1982". Since then, a large amount of work on bovine animals has confirmed the importance of increasing galactopoiesis following daily treatments of dairy cows with bGH during entire lactation periods (Baird L. S. et al., "J. Dairy Sci., 69 (supp 1) 118 (Abst.) 1986"; Bauman D. E. et al., "J. Dairy Sci., 68 1352-62 (1985)"; Chapula W. and Schneider P. L., "Proc. Univ. Guelph Nutr. Conf. pp 106-21 (1986)"; Hutchinson C. F. et al, ("J. Dairy Sci., 69 (supp 1) 152 (Abst.) (1986)"; Mollett T. A. et al., "J. Dairy Sci., 69 (supp 1) 118 (Abst.) (1986)"; and Soderhol M. C. G. et al. (J. Dairy Sci., 69 (supp 1), 152 (Abst.) (1986)".

After analysis of these results, adjusted to a milk with a fat content of 3.5%, a milk production increased by 16, 19 and 22% is observed for respective treatments of 12.5, 25 and 50 mg of bGH per day. In addition, the increase in the feed intake in the treated cows is not proportional to the improvement in milk productivity, so that the nutritional efficiency (expressed in kilograms of milk with a fat content of 3.5% per kilogram of dry matter ingested) is increased by 13.8, 16.8 and 15.3%, respectively, in animals receiving 12.5, 25 or 50 mg of bGH/day for a long period.

The factor stimulating the secretion of human growth hormone has been isolated and characterized, and it is now synthesized industrially. This factor will be designated hereinafter by the abbreviation "hGRF". Its natural form contains 44 amino acids. The form containing 29 amino acids which is obtained after deletion of the C-terminal portion of the molecule, and whose biological activity is similar to that of the intact molecule, is also known. In both cases, human GRF differs from the corresponding bovine and ovine GRF only by a very small number of amino acids.

Moreover, the production of a slow form is easier to achieve for hGRF than for human growth hormone or human antehypophyseal hormone (hereinafter designated by the abbreviation "hGH", once again because of the smaller size of the molecule and a smaller number of active sites to be protected during the production of an "implant".

hGRF is currently used in human medicine as an hGH hormone releasing factor (Guillemin R., Bazeau P., Bohlen P., Esch F., Ling N., Wehrenberg W. B., "Growth hormone releasing factor from a human pancreatic tumor that caused aeromegaly, Science, Wash. D.C., 218, 585.7, 1982").

Patent Application FR-A-2,594,832 shows that the stimulation of protein anabolism due to growth hormone endows GRF with a particularly promising future for promoting meat and milk production in livestock. The subject of this application consists of derivatives of growth hormone releasing factor (GRF) possessing modified amino acids, these derivatives being applicable for promoting the growth of a human being or bovine, porcine or ovine animal. However, in this earlier application, there is no particular description regarding the details of the treatment.

The same comment may be made in relation to Patent Application EU 137,689, which relates to GRF analogs and their production, as well as to a composition for accelerating the growth of warm-blooded animals (not including man), for accelerating the growth and/or milk production of animals of bovine or caprine species, for accelerating the growth of animals of the porcine species and for accelerating the growth and/or milk production of animals of the ovine species. In the case of the administration of these substances to animals, the activity of the said substances is transitory, and ceases as soon as the treatment is interrupted.

The same observations may be made in relation to other documents illustrating the prior art, namely:

Commonwealth Agriculture Bank 86302113 CAB 860198070; D. Petitclerc et al, Sanofi Recherche 1986 p. 343-358.

Commonwealth Agriculture Bank 87355649 CAB 870107052; P. Dubreuil et al, Reproduction, nutrition, development Vol. 27 no. 28, 1987, p. 601-603, Biological Abstracts no. 33122957; H. Lapierre et al, Journal of Animal Science, 1987, vol. 65, no suppl. 1, p. 429, Biological Abstracts no. 33095008 and 33095009; D. Petitclerc et al, Journal of Dairy Science, 1987, vol. 70, no. suppl. 1, p. 178.

It is thus observed that none of the documents illustrating the prior art discloses the treatment of mammals, including man, with hGRF for short periods of time during pregnancy, the effect produced being lasting and extending throughout the lactation period.

The problem to which the present invention provides a solution is, in particular, that of obtaining an improvement in milk output by a treatment of the animals for short periods of time during pregnancy, in order to avoid daily treatment, which represents a drawback from both the economic standpoint and the practical standpoint.

It has now been found—and this constitutes the basis of the present invention—that the administration of hGRF, its active fragments or corresponding analogs to females during pregnancy and, more precisely, for a short period at a specified point in the pregnancy, enabled the abovementioned problem to be solved. The active fragments correspond to hGRF molecules which are truncated but contain the activity. Thus, the form containing 29 amino acids, which has been described above and which will be designated hereinafter by the abbreviation "hGRF (1-29)", constitutes an important form of the family of active substances according to the invention.

As regards the analogs, also mentioned above, of hGRF or of its active fragments, they correspond, respectively, to hGRF and to the active fragments in which at least one amino acid has been substituted.

In addition, during the work which led to the present invention, it was found that the administration of the abovementioned active principles, once again during pregnancy, but at another point in the latter, and once again over a relatively short period, led to an increase in the birth weight of the newborn and to an improvement in their postnatal growth, compared with animals born of untreated mothers. Cumulative treatment during both of the abovementioned periods has also been carried out.

To this advantage of a treatment over a short period, or over short periods, there is added the fact that the abovementioned substances, and especially hGRF (1-29) is a specific molecule, and hence applicable to all species, and which is part of the protein hormones, and hence completely degraded by the body.

Among the many special applications which may be mentioned for the present invention, it may be pointed out that, in sows, the outcome is an increase in weight of the piglets and a decrease in mortality through hypotrophy; and the production of earlier puberty in ewes and cows (it is thus possible to bring forward the date at which reproduction may be commenced). In man, the advantage of being able, without adverse effects on the mother and child, to avoid the birth of a hypotrophic child is worthy of note.

The subject of the present invention is hence, in the first place, a method for increasing milk production in mammals including man, and/or for increasing the birth weight of their newborn and improving postnatal growth, according to which the female mammal is supplied during pregnancy with an effective amount of hGRF or of one of its analogs, or alternatively of an active fragment of hGRF or of one of its analogs.

In a preferred embodiment, hGRF is used in its form containing 29 amino acids (human GRF 1-29), or an analog of this form.

The subject of the present invention is also a composition intended for carrying out the abovementioned method with a view to being supplied to mammals, including man, for increasing milk production and/or for increasing the birth weight of their newborn and improving postnatal growth, the said composition containing, as active principle, hGRF or one of its analogs, or alternatively an active fragment of hGRF or of one of its analogs, said active principle being combined with a physiologically acceptable vehicle.

In particular, this composition is presented in an injectable form, dissolved in a physiological solution.

The amount of active principle to be injected varies according to the species. In the case of ewes, it is preferably of the order of 25 μg/kg of body weight/day, administered subcutaneously. The composition will hence be presented accordingly.

According to a special embodiment, the active principle of the composition can be put into a form that permits its slow release in the body.

The subject of the invention is also:

a method for increasing milk production in mammals, according to which the female mammal is supplied, over a period of the order of 10 to 20 days, on completion of two-thirds of the gestation period, with an effective amount of hGRF or of one of its analogs, or alternatively of an active fragment of hGRF or of one of its analogs.

a method for increasing the birth weight of newborn mammals including man, and improving postnatal growth, according to which the female mammal is supplied, over a period of the order of 10 to 20 days immediately preceding parturition, with an effective amount of hGRF or of one of its analogs, or alternatively of an active fragment of hGRF or of one of its analogs.

a method for increasing milk production in mammals including man, and/or for increasing the birth weight of their newborn and improving postnatal growth, according to which the female mammal is supplied, over a period of the order of 10 to 20 days, on completion of two-thirds of the gestation period, and over a period of the order of 10 to 20 days immediately preceding parturition, with an effective amount of hGRF or of one of its analogs, or alternatively of an active fragment of GRF or of one of its analogs.

The subject of the present invention is also the use of hGRF or of one of its analogs, or alternatively of an active fragment of hGRF or of one of its analogs, for manufacturing a composition intended for increasing milk production in mammals, including man, and/or for increasing the birth weight of their newborn and improving their postnatal growth.

The invention is applicable most especially to animals of ovine, caprine, bovine or porcine species.

The experiments reported below illustrate the invention and the advantageous results thereby obtained.

A—EFFECTS OF THE ADMINISTRATION OF hGRF (1-29) TO EWES AT THE END OF THE GESTATION PERIOD, ON FETAL GROWTH

1—Experimental protocol 30 gravid ewes which were at the 135th day of gestation were distributed in two batches of 15 ewes each, account being taken of the number of fetuses assumed to be present in the uteri and of the earlier milk outputs, all the ewes being multiparous.

Batch A, which receives no treatment, serves as control batch. Batch B receives 1.5 mg of hGRF (1-29) (equivalent to approximately 20 μg per kg of body weight) subcutaneously twice daily, at 8.00 hours and 14.00 hours, from day 137 of gestation up to the day of littering (which varied between day 145 and day 147, depending on the ewe). The administration of hGRF (1-29) is stopped as soon as parturition takes place. In all the animals, lambing is induced by the administration of 9 α-fluoro-11β,17α,21-trihydroxy-16α-methyl-1,4-pregnadiene-3,20-dione (proposed under the INN of dexamethasone) on the basis of 16 mg intramuscularly at 20.00 hours on day 144 of gestation.

The birth weights of the lambs born of mothers of the two batches A and B were compared.

2—Results

The following observations were made:

The administration of hGRF (1-29) induces, at the doses used, a discharge of growth hormone (hereinafter GH) of large magnitude, the duration of which is approximately 5 hours after the subcutaneous injection. This discharge is the same in nature after the morning injection and after that of the afternoon. Moreover, the response is magnified as the term of the pregnancy is approached. This is shown in FIG. 1 of the attached drawings, which represents the OGH hormone assay in terms of the time of day (mean over 15 ewes) on day 138 and on day 146 of gestation.

Legend to FIG. 1 o—o hGRF (1-29) administered as described on D138
o—o hGRF (1-29) administered as described on D146.

Under these conditions, the animals of batch B have a level of circulating GH during the day which is from 10 to 15 times as high as that of batch A.

The parturitions proceeded under the same conditions for both batches, the prepartum administration of hGRF (1-29) not modifying the dates of the lambing.

The birth weight of the lambs born of treated mothers (batch B, n=20) is very significantly (p≃0.003) higher than that of the lambs derived from the control batch (batch A, n=21), since the lambs born of ewes of batch 8 weigh 4.17±0.13 kg, compared with 3.61±0.14 kg for the lambs born of mothers of batch A.

This experimental study demonstrated that the treatment of ewes with hGRF (1-29) in the immediate prepartum period induces a more rapid in utero growth of the fetuses.

B—USE OF hGRF (1-29) ON COMPLETION OF TWO-THIRDS OF THE GESTATION PERIOD AND/OR AT THE END OF THE GESTATION PERIOD IN EWES: EFFECT ON FETAL GROWTH AND ON SUBSEQUENT GROWTH OF THE YOUNG EWES

1—Experimental protocol 48 multiparous gravid ewes were distributed in four batches of 12 ewes each, account being taken of the earlier milk productions and of the anticipated parity (OCS—Ovine Chorionic Somatotropin—assay).

The first batch forms the control batch, the ewes receiving no treatment.

The other three batches receive 1.5 mg of hGRF (1-29) subcutaneously twice daily;

from day 105 to day 115 of gestation for the second batch, which will be designated hereinafter as batch "GRF1";

from day 137 of gestation to littering for the third batch, which will be designated hereinafter as batch "GRF2"; and from day 105 to day 115 of gestation and from day 137 of gestation to littering for the fourth batch, which will be designated hereinafter as batch "GRF1+2".

As in the above study, the administration of hGRF (1-29) is stopped as soon as parturition takes place, and lambing is induced by the administration of dexamethasone on day 145 of gestation, under the conditions described above.

After parturition, the milk production of the ewes was measured twice daily, and the growth of the lambs, which received an artificial milk-feed supplied "ad libitum", was followed, the lambs receiving no growth adjuvant treatment.

2—Results a—Birth weight

The analysis concerned only twin lambs, distributed as follows:

Control n=12
GRF 2 n=12
GRF1 n=16
GRF1+2 n=12

Figure 2:
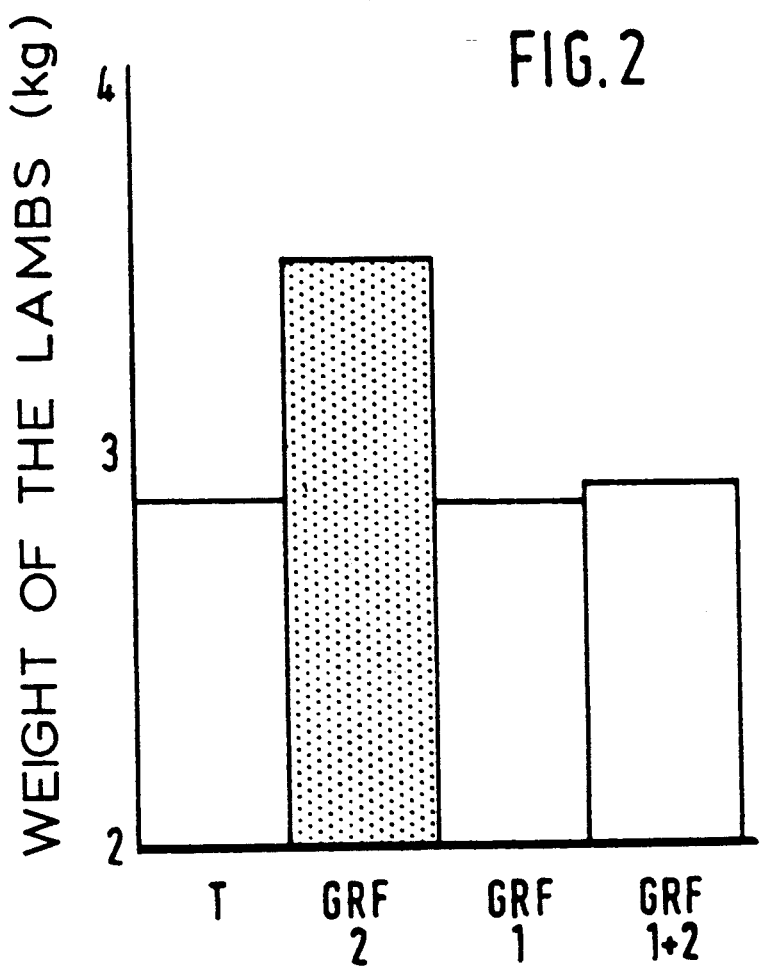

FIG. 2 of the attached drawings, which shows the diagram of the birth weight of the lambs derived from the four batches, shows that the treatment performed induces a larger in utero growth of the fetuses in the ewes of batch GRF2, since the mean value of the birth weight is 3.54 kg (p≧0.007) for this batch, whereas it is only 2.91 kg for the lambs born of the "control" mothers.

FIG. 2 also shows that the lambs derived from batches GRF1 and GRF1+2 have a birth weight substantially similar to that of the lambs born of the "control" mothers.

b—Growth of the lambs

Figure 3:
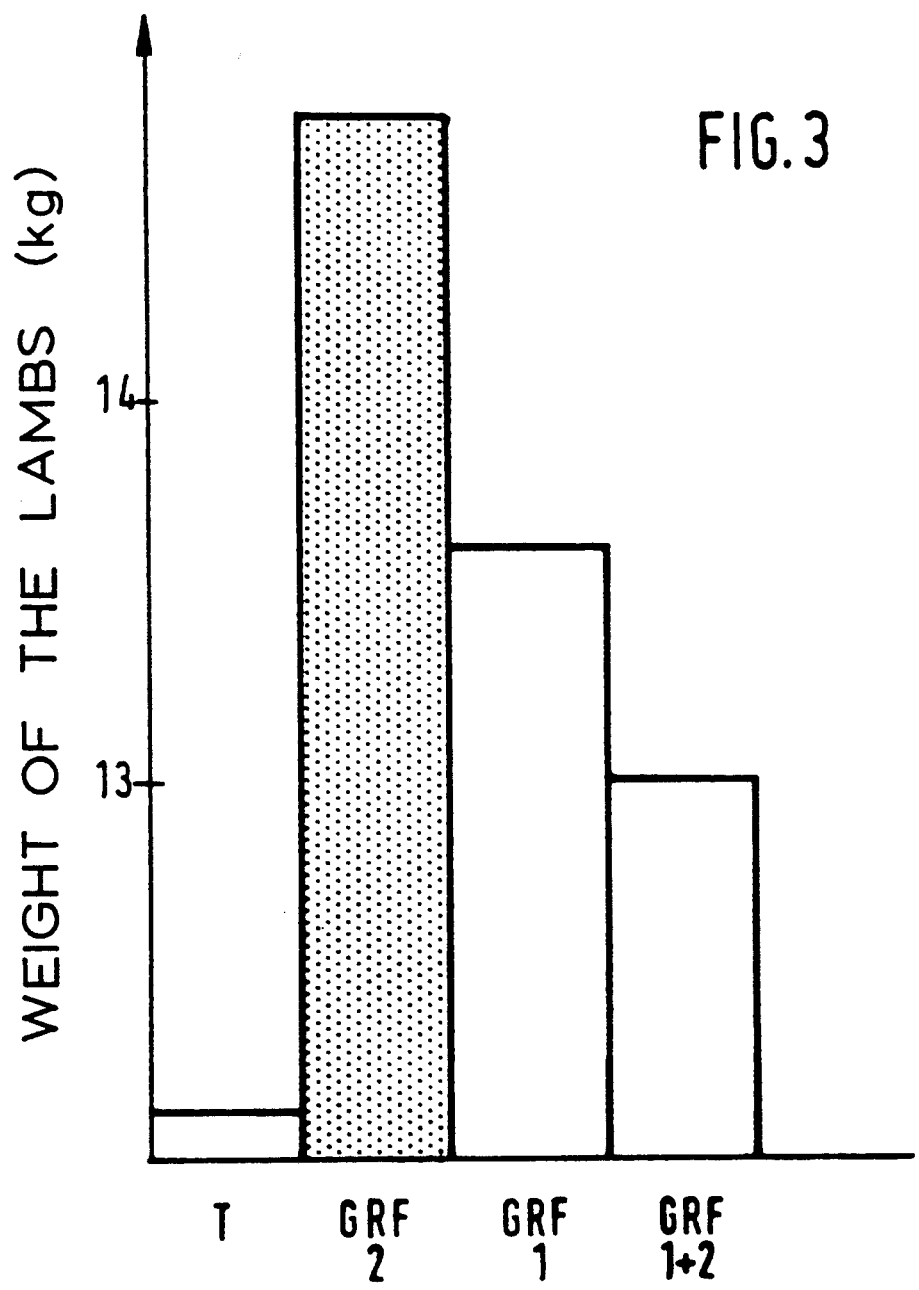

At the age of 30 days, after variance analysis taking birth weight as covariable, a larger growth of all the lambs born of the mothers of batch GRF2 was observed. This is shown in FIG. 3, which is an illustration similar to that of FIG. 4, enabling the weights of the lambs born of the mothers of the four batches to be compared at the age of 30 days. Table 1 below complements this FIG. 3.

TABLE 1

| Batch | Number of lambs | Weight of the Lambs at 30 days |
|---|---|---|
| Control | 7 | 12.12 ± 0.7 kg |
| GRF2 | 12 | 14.73 ± 0.53 kg (p > 0.006) |
| GRF1 | 14 | 13.6 ± 0.5 kg (p > 0.09) |
| GRF1 + 2 | 10 | 13 ± 0.66 kg (ns) |

It is observed that the treatment with hGRF (1-29) of the mothers between days 137 and 147 of gestation induces a larger postnatal growth. Thus the growth of these lambs, even when corrected by the covariable represented by the birth weight, is larger, since it exceeds by 21% the weight of the controls at 30 days.

Moreover, when the ewes have been treated with hGRF (1-29) between days 105 and 115 of their gestation, they give birth to lambs whose birth weight is of the same order as those of the lambs born of the "control" mothers but, at 30 days, the growth of these lambs remains still greater, of the order of 11%, than the growth of the lambs born of the "control" mothers.

3—Milk production

After a variance analysis, taking the earlier production as covariable, and after correction taking into account the parity (number of lambs per pregnancy) during the lactation in progress and during the reference lactation, the results for the milk production were compared between the control batches and batches "GRF1" and "GRF2". From the results obtained over five weeks of lactation, the curves of FIGS. 4 and 5 were plotted, the source data being reported in Table 2 below.

TABLE 2

Figure 4:
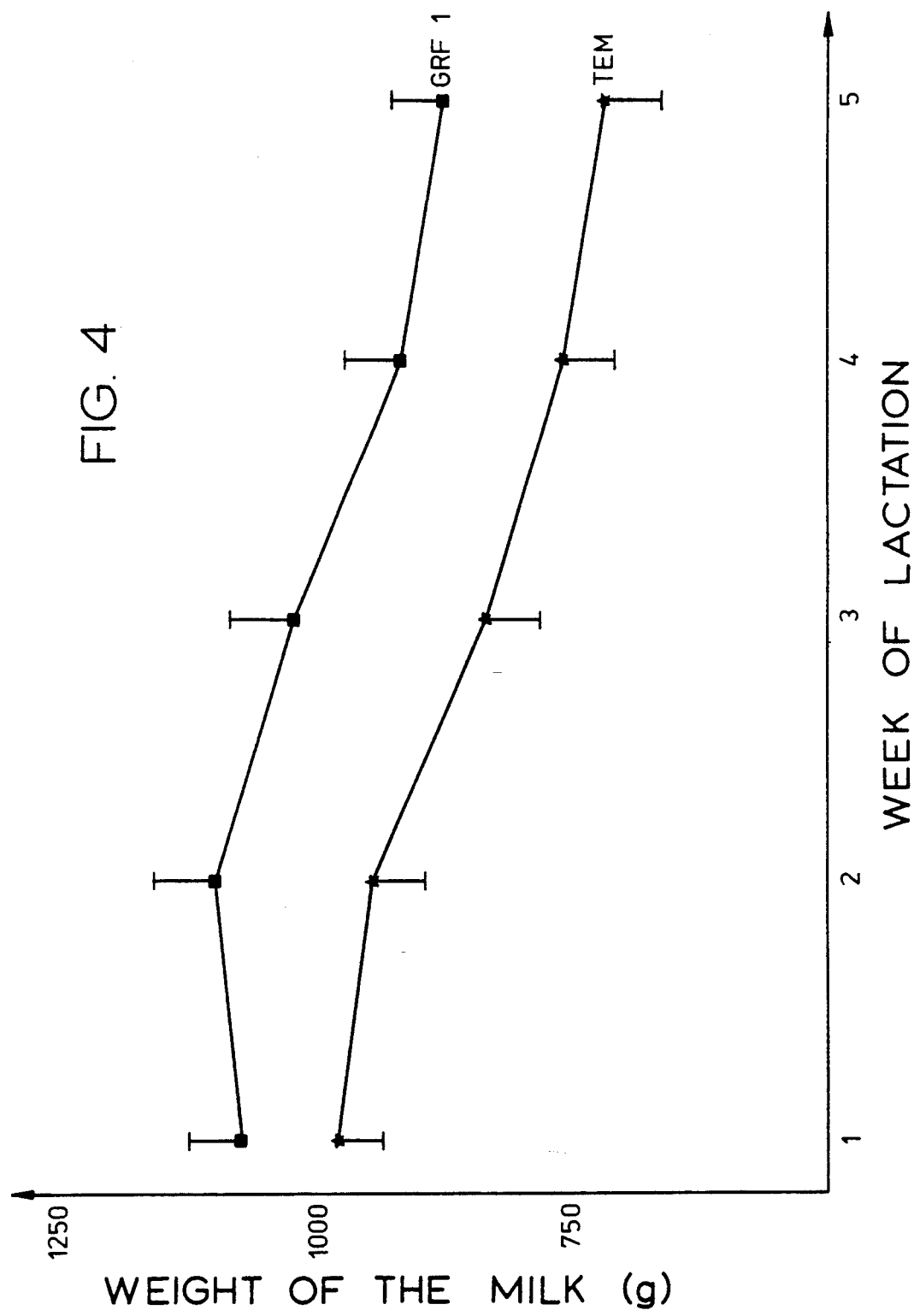
Figure 5:
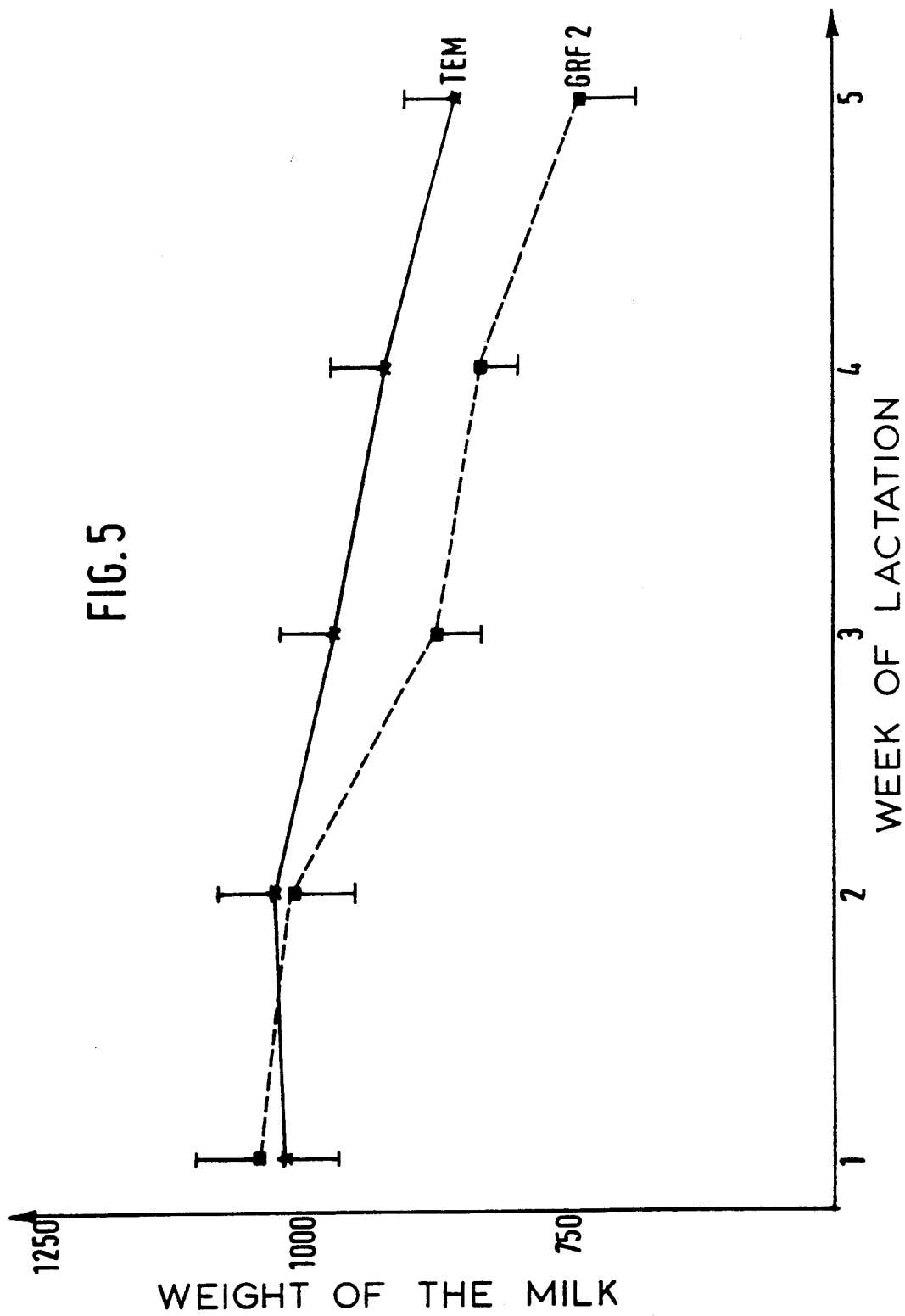

| Milk production | | |
|---|---|---|
| Week of | FIG. 4 | |
| lactation | Control | GRF1 |
| 1 | 980 ± 70 | 1075 ± 50 ns |
| 2 | 950 ± 60 | 1090 ± 70 ns |
| 3 | 845 ± 50 | 1025 ± 60p ≧ 0.07 |
| 4 | 760 ± 45 | 920 ± 60p ≧ 0.1 |
| 5 | 720 ± 50 | 880 ± 50p ≧ 0.08 |
| Week of | FIG. 5 | |
| lactation | Control | GRF2 |
| 1 | 1020 ± 50 | 1050 ± 60 ns |
| 2 | 1025 ± 60 | 1010 ± 50 ns |
| 3 | 975 ± 50 | 855 ± 50 ns |
| 4 | 925 ± 50 | 840 ± 40 ns |
| 5 | 860 ± 50 | 745 ± 60 ns |

It is observed that the milk production of the ewes treated between days 105 and 115 of gestation (batch "GRF1") is greater than that of the "control" ewes (more than 23% during the fifth week of lactation with $p \geq 0.08$).

The overall outcome would hence suggest that treatment with hGRF (1-29) between days 105 and 115 of gestation increased mammogenesis in the treated ewes. These results confirm those obtained with the induction of lactation, and show that GH is indeed an important hormone in the process of mammogenesis in pregnancy, apparently acting independently of the placental hormone OPL.

The role of GH as a factor regulating the orientation of the "energy fluxes" towards the mammary gland or towards the uterus, depending on the period of stimulation by hGRF, is demonstrated, and this means that a ewe in which a strong mammogenesis has been induced will not give birth to a lamb having a higher weight; conversely, a ewe which has been stimulated so as to obtain a larger lamb will have a decreased milk production.

What is claimed is:

1. A method for increasing milk production in female mammals used in milk production, including man, according to which the female mammal is supplied, over a period of the order of 10 to 20 days, on completion of two-thirds of the gestation period, with an effective amount of hGRF or of one of its analogs, or alternatively of an active fragment of hGRF or of one of its analogs.

2. A method for increasing the birth weight of newborn mammals including man, and improving postnatal growth, according to which the female mammal is supplied, over a period of the order of 10 to 20 days immediately preceding parturition, with an effective amount of hGRF or of one of its analogs, or alternatively of an active fragment of hGRF or of one of its analogs.

3. A method for increasing milk production in mammals including man, and/or for increasing the birth weight of their newborn and improving postnatal growth, according to which the female mammal is supplied, over a period of the order of 10 to 20 days, on completion of two-thirds of the gestation period, and over a period of the order of 10 to 20 days immediately preceding parturition, with an effective amount of hGRF or of one of its analogs, or alternatively of an active fragment of GRF or of one of its analogs.

4. The method as claimed in any one of claims 1 to 3, in which the active fragment of hGRF which contains 29 amino acids is used.

5. The method as claimed in any one of claims 1 to 3, according to which animals of ovine, caprine, bovine or porcine species are treated.

6. The method as claimed in claim 4, according to which animals of ovine, caprine, bovine or porcine species are treated.

* * * * *